United States Patent [19]

Lynnworth

[11] Patent Number: 4,783,997

[45] Date of Patent: Nov. 15, 1988

[54] ULTRASONIC TRANSDUCERS FOR HIGH TEMPERATURE APPLICATIONS

[75] Inventor: Lawrence C. Lynnworth, Waltham, Mass.

[73] Assignee: Panametrics, Inc., Waltham, Mass.

[21] Appl. No.: 19,020

[22] Filed: Feb. 26, 1987

[51] Int. Cl.⁴ .............................................. G01N 29/00
[52] U.S. Cl. .................................... 73/644; 73/861.18
[58] Field of Search ...................... 73/644, 632, 861.18, 73/597, 861.27, 861.28

[56] References Cited

U.S. PATENT DOCUMENTS

| | | | |
|---|---|---|---|
| 3,242,723 | 3/1966 | Evans | 73/644 |
| 3,302,044 | 1/1967 | Lynnworth et al. | 73/644 |
| 3,350,923 | 11/1967 | Cross | 73/644 |
| 3,512,400 | 5/1970 | Lynnworth | 73/597 |
| 3,534,609 | 10/1970 | Grenfell et al. | 73/597 |
| 3,890,423 | 6/1975 | Zacharias | 73/644 |
| 4,014,211 | 3/1977 | Araki et al. | 73/644 |
| 4,392,380 | 7/1983 | Caines | 73/644 |
| 4,556,814 | 12/1985 | Ito et al. | 73/644 |
| 4,567,770 | 2/1986 | Rumbold et al. | 73/644 |

FOREIGN PATENT DOCUMENTS

| | | | |
|---|---|---|---|
| 1411238 | 9/1965 | France | 73/644 |
| 732083 | 6/1955 | United Kingdom | 73/644 |

OTHER PUBLICATIONS

Lynnworth et al., "Screw Pressure Coupler and Mode Converter", NDT Communications, (Gordon and Breach, UK, 1984).

Allen Sather, "Ultrasonic Buffer-Rod Technique for the High-Temperature Measurement of the Elastic Moduli of Short Specimens," *The Journal of the Acoustical Society of America*, vol. 43, No. 6, pp. 1291-1294, (1968).

Visintini et al., presented at the IEEE Ultrasonic Symposium, Nov. 17-19, 1986, "Analysis of Broadband Lamb-Wave Delay Lines."

Youngdahl et al., (1978), Ultrasonics Symposium Proceedings IEEE Cat. #78CH 1344-1SU, "Development of Ultrasonic Techniques for Remote Monitoring of Erosive Wear in Coal-Conversion Systems," pp. 305-310.

Lynnworth, "Ultrasonic Flowmeters," in Physical Acoustics, edited by Warren P. Mason et al., vol. XIV 1979 pp. 472-475.

Anderson, et al., "Detecting Acoustic Emission in Large Liquid Metal Cooled Fast Breeder Reactors" in *Acoustic Emissions* (1972), pp. 250-269.

Emmanuel P. Papadakis, (1972), *Mater. Sci. Eng.* 10, "Tabulation of the Coefficients of a Quadratic Function for the Thermal Expansion of Various Alloys and Other Engineering Materials", pp. 195-203.

Yada et al., (1981), "A Clamp-On Ultrasonic Flow Meter for High Temperature Fluids in Small Conduits", in *FLOW: Its Measurement and Control in Science and Industry*, vol. 2, ed. by William W. Durgin, pp. 549-560.

*Primary Examiner*—John Chapman
*Attorney, Agent, or Firm*—Lahive & Cockfield

[57] ABSTRACT

A clamp-on ultrasonic transducer assembly for making ultrasonic measurements on solid materials in a temperature far removed from ambient. An electroacoustic transducer is coupled to the solid surface through an elongated buffer element enclosed within a housing which is mechanically coupled to the buffer element only in the region of contact between the buffer and the solid material to be measured.

24 Claims, 5 Drawing Sheets

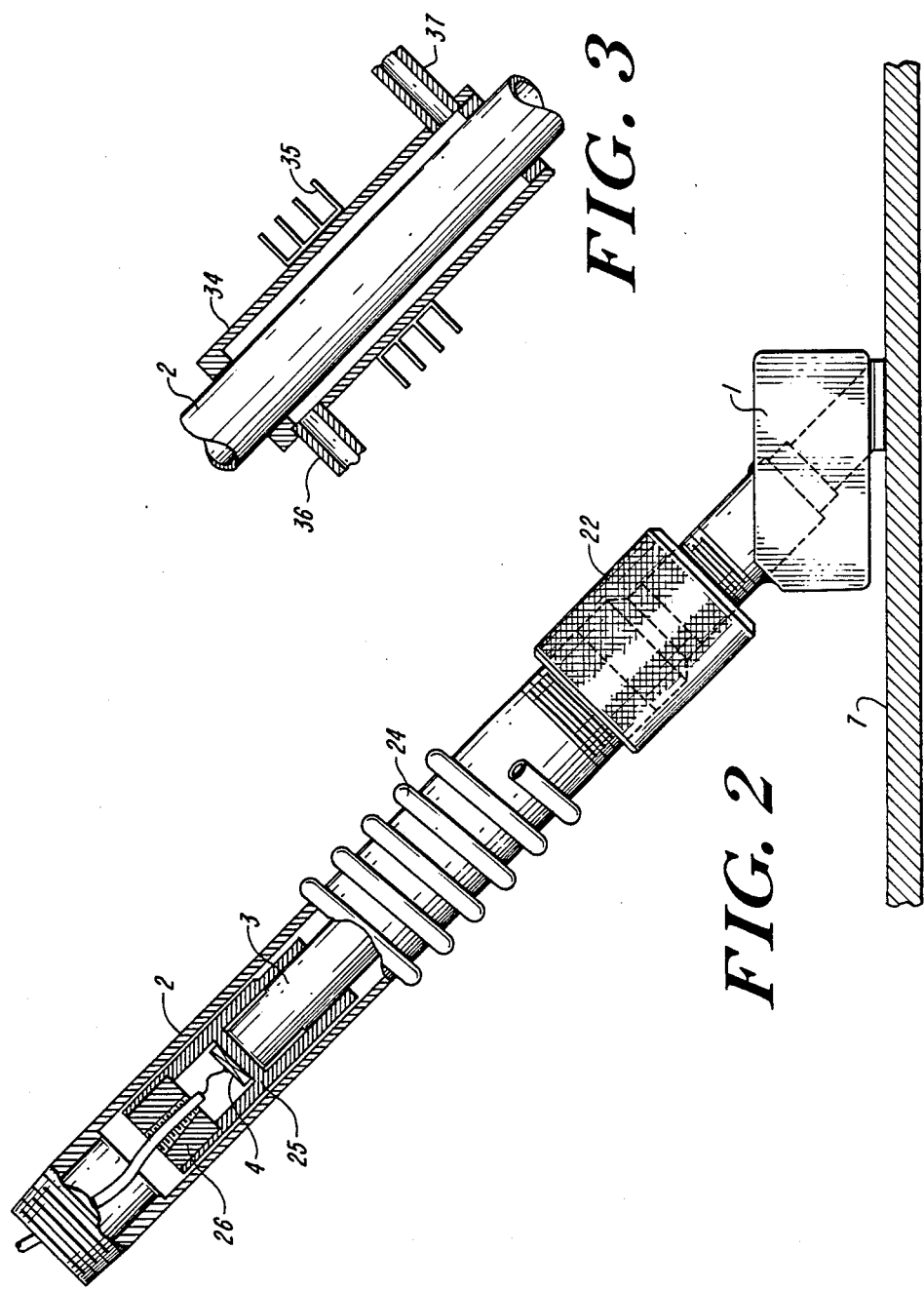

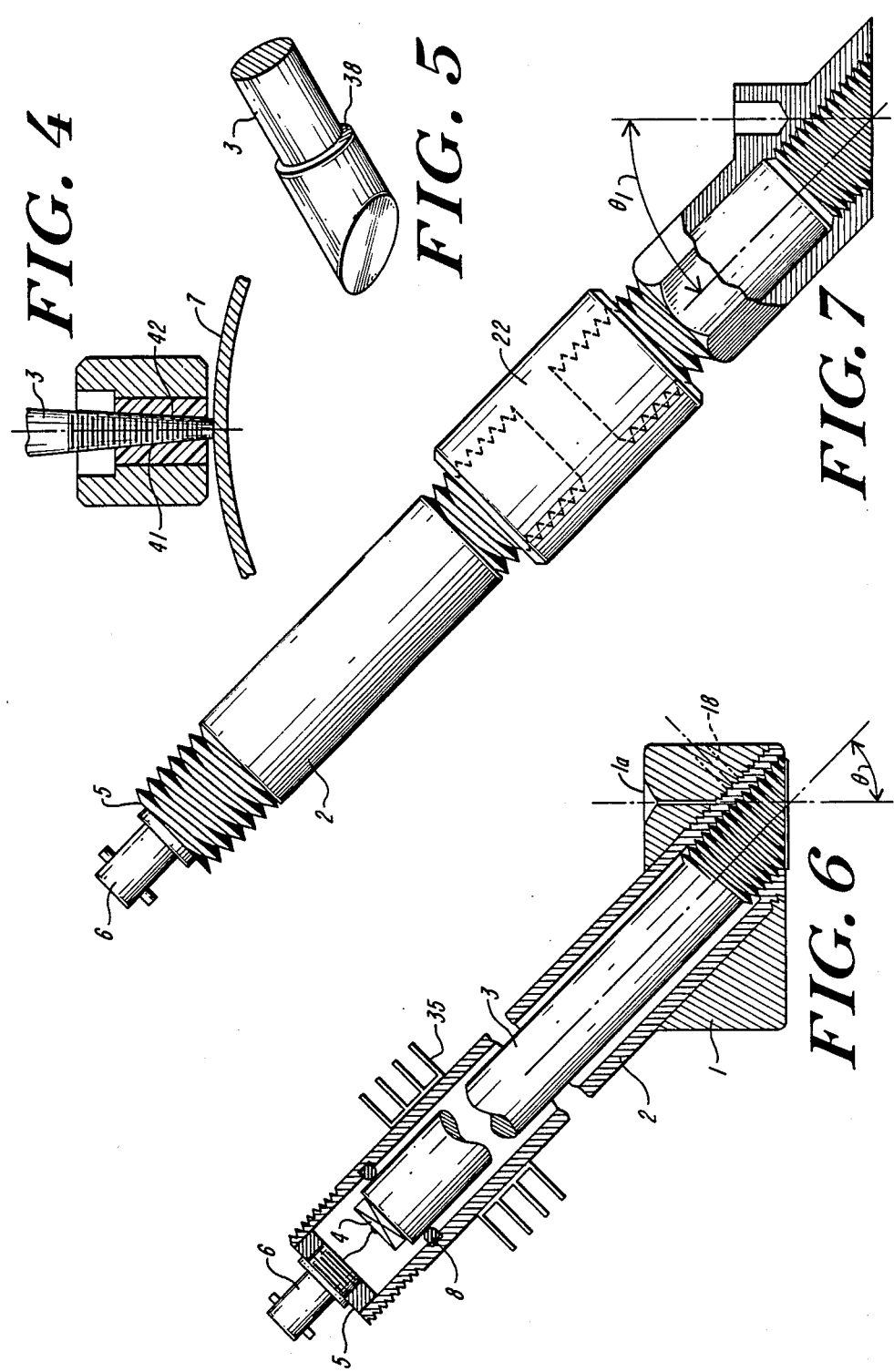

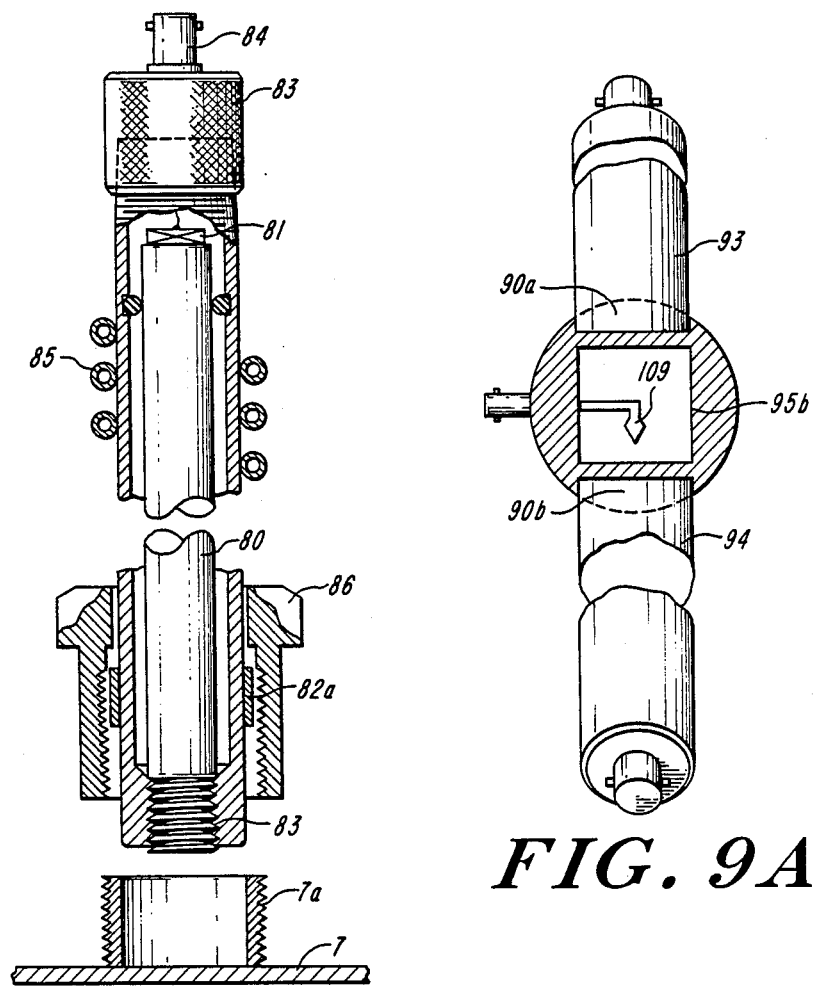
FIG. 8
FIG. 9A
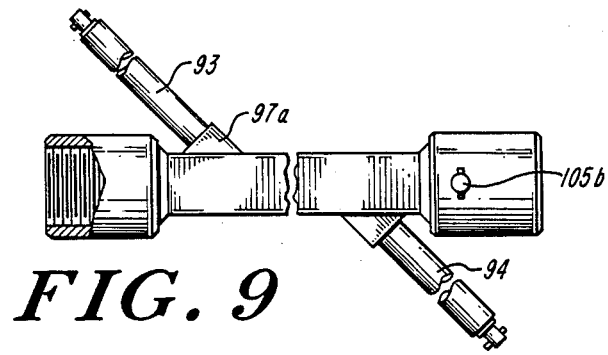
FIG. 9

ULTRASONIC TRANSDUCERS FOR HIGH TEMPERATURE APPLICATIONS

FIELD OF THE INVENTION

This invention relates in general to ultrasonic transducers and more particularly to ultrasonic transducer assemblies for use on materials which are far removed from ambient temperature.

BACKGROUND OF THE INVENTION

Ultrasonic transducer assemblies have found wide use in a number of measurement situations. The ultrasonic transducer itself is typically formed of an electroacoustical transducer producing bulk ultrasonic waves in response to controlled electrical signals. The transmission characteristics, either velocity or attenuation, of the ultrasonic waves through the medium being measured provide an indication of various key characteristics. One very common application is the application of ultrasonic signals to measure the flow of materials through pipes or other conduits. In this application it is often desirable to employ a clamp-on transducer which can be permanently or temporarily attached or coupled to the outer wall of the pipe. Depending in part upon the angle of incidence of the waves propagated from the electroacoustical transducer, the waves as generated may be used for measurement or alternatively Rayleigh, Lamb, or other waves generated by mode conversion at the pipe wall or the fluid pipe wall interface, may be employed.

A single transducer assembly can be used to Perform the measurement employing a technique involving reflection of the ultrasonic waves from a surface within the pipe and measuring the received reflected wave. Many times, however, in measurement of fluid characteristics within a pipe a pair of transducers are employed for generating a signal at one transducer and receiving it at the other. In some arrangements the transmitter and receiver functions of the pair of transducers are alternated in time.

In the use of clamp-on transducers on pipe walls where the pipe is at either very high temperature or low temperature, problems arise due to the limited temperature range over which the usual electroacoustical transducers can operate.

One previous solution to this problem was to use a LiNbO₃ piezoelectric element as the transducer. However, this element requires an oxygen-bearing atmosphere at high temperature to avoid decomposing, and also suffers from differential expansion coefficients along different axes. In a number of transducer systems it has been conventional to use a buffer element providing a solid material forming an acoustic transmission path between the electroacoustic transducer and the surface of the pipe or other material into which the acoustic wave is to be transmitted. Requirements of acoustic transmission characteristics and strength have dictated the choice of these materials, which, for the most part, have been metallic. Such buffers are, of course, good heat conductors and hence do not serve adequately to isolate the electroacoustic element from high temperature surfaces when these are the material to be contacted for measurement. In addition metallic buffers often do not provide acoustical properties (low sound speed, moderately high attenuation) that are particularly desirable in a buffer especially where certain mode conversions in the pipe or other adjacent solid medium are desired.

SUMMARY OF THE INVENTION

Broadly speaking this invention provides a transducer assembly for utilization in transmitting ultrasonic waves into solid materials at temperatures well removed from ambient temperature. The assembly includes an electroacoustic transducer, which typically operates over a limited temperature range. The transducer is coupled to a material surface through an elongated buffer element which serves to couple ultrasonic waves effectively to the surface of the solid material, while at the same time providing a temperature gradient along its length sufficient to thermally isolate the transducer from the high or low temperatures at that surface. The buffer and the transducer are enclosed within a housing, usually formed of stainless steel, which provides both mechanical strength (including creep resistance) for Pressure coupling the transducer to the surface while electrically shielding the RF signals generated by the transducer. The shield also provides corrosion resistance. Corrosion resistant alloys like SS316 are convenient as the metal for the shield.

The key to the present invention is the fact that the housing is coupled mechanically through the buffer only over a very short axial distance and at a position close to the interface between the buffer element and the solid material to be contacted. In this arrangement the required high Pressure necessary for coupling the ultrasonic waves into the pipe surface is achieved, yet the mechanical separation between the elongated buffer element and the housing over most of the length of the buffer element allows the buffer element to be formed of a material which has a significantly different thermal expansion characteristic than that of the housing. In this way the material for the shield and the material for the buffer can each be selected to optimize their individual properties according to their different tasks or functions. In this invention the buffer is Preferably formed of a non-metallic substance which is characterized by high attenuation and dispersion of ultrasonic waves, sound speed appropriate for producing the desired mode conversion at the pipe wall in cases of oblique incidence, and a small temperature dependence of sound velocity and attenuation. The use of high attenuation material allows a correspondingly high frequency of interrogation, for example, 1 kHz. One particularly suitable buffer material has been found to be graphite in forms such as ATJ and CMG, while SS316 is typically appropriate as the shield material.

DESCRIPTION OF THE DRAWINGS

In the drawings:

FIG. 2 is an illustration in cross-sectional view of a second embodiment of a transducer assembly in accordance with the principles of this invention;

FIG. 3 is cross-sectional view of an alternative form of heat exchanger for use in the embodiment of FIG. 2;

FIG. 4 is a cross-sectional view of a specific geometrical form of buffer useful in the practice of this invention;

FIG. 5 is a perspective view of a portion of a buffer rod suitable for use in the embodiment of FIG. 1;

FIGS. 6, 7 and 8 illustrate alternative embodiments of transducer assemblies constructed in accordance with the principles of this invention;

FIG. 9 is a general perspective view of a transducer assembly in accordance with the principles of this invention including a specific conduit insert;

FIG. 9A is an end cross-sectional view of the embodiment illustrated in FIG. 9;

DESCRIPTION OF PREFERRED EMBODIMENTS

Figure 1:
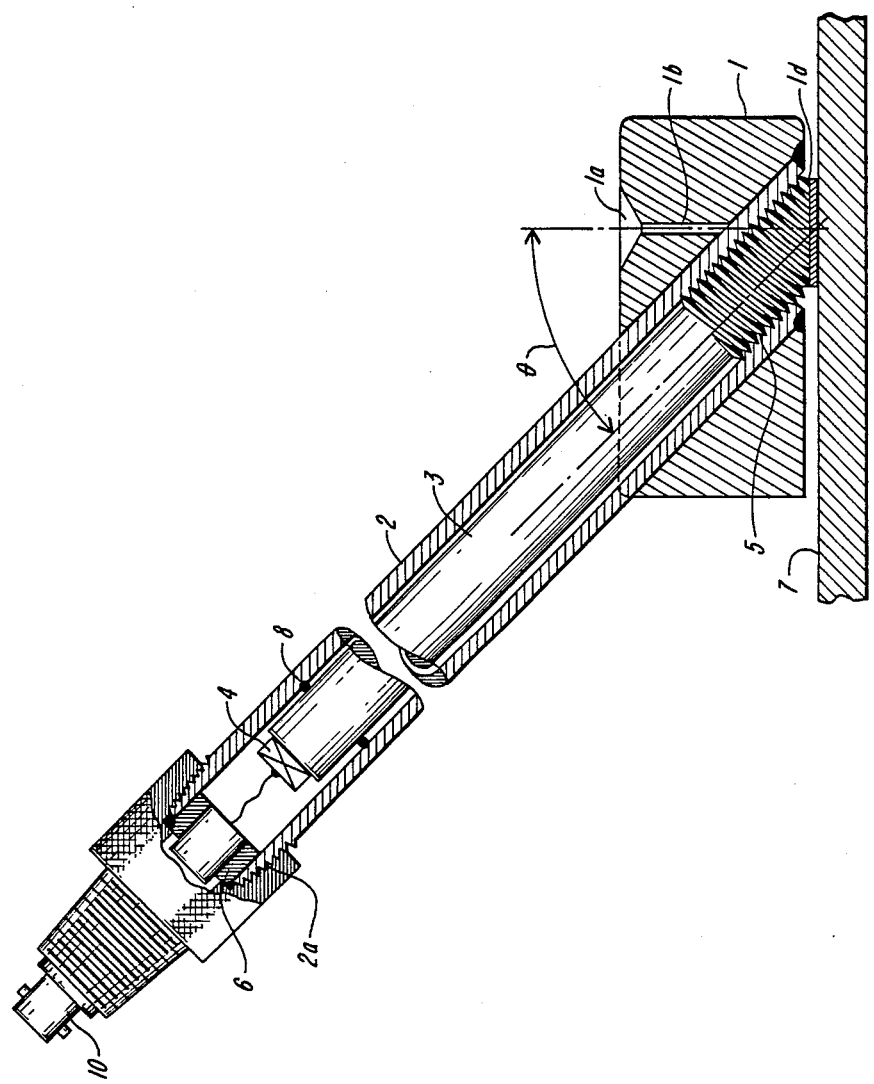
FIG. 1 is a cross-sectional illustration of a transducer assembly constructed in accordance with the principles of this invention.

With reference now to FIG. 1 the transducer assembly is shown to include an electroacoustic transducer soldered or otherwise connected to an elongate, generally cylindrical buffer element 3 of graphite, such as ATJ or CMG graphite. In order to facilitate this connection the end face of the buffer element may be plated with nickel. The buffer is shown formed with a threaded portion 5 at one end. There is an oblique face for making direct contact with the material surface 7. The material surface 7 is typically a wall of a pipe containing fluid, the characteristics of which are to be determined by ultrasonic interrogation. A generally cylindrical enclosure 2 surrounds the buffer rod and extends beyond the electroacoustical transducer 4 to support an end cap 6 into which is fitted a standard electrical connector 10 such as a standard BNC connector. This connector provides for an electrical connection directly to the electroacoustic transducer 4. The end of the cylindrical housing 2 is enclosed within a generally block-shaped structure 1. The block type structure 1 and the enclosing tube 2 are usually formed of a material having an appropriate electrical shielding effect, as well as mechanical strength and tolerance for the extremes of high or low temperatures which may be present at the surface of the material 7. In many situations the environment in which the transducer assembly is operated may also be chemically active and hence the material must also be a suitable material for this circumstance. The stainless steel alloy SS316 has ben found to meet all these requirements.

While graphite has been described as the preferred material for the buffer element 3, other suitable creep resistant (usually non-metallic) materials may be employed. As examples of non-plastic, non-ferrous creep resistant buffer materials, nitrides such as boron nitride, oxides such as alumina, and certain composites may be used. The relative dimensions of the housing 2 and the buffer element 3 are such as to allow a clearance between them. For example, if the buffer diameter is in the order of fifteen to twenty mm, the housing 2 may typically be formed of a ¾" pipe nipple approximately 150 mm long. This housing 2 can then be screwed or welded to the block 1 near one of its ends and threaded at the other end. In this example, a suitable outside dimension for the block may be about 25×25×50 mm. Near the transducer end of the buffer 3 a resilient adhesive, or rubber-like O-ring 8 may be installed between the buffer 3 and the housing 2 as an antirotation and/or damping means.

As above stated the buffer 3 is coupled to the adjacent solid medium 7 such that it is effectively coupled for transmission of acoustic ultrasonic waves over wide temperature extremes. Where the circumstances are such that the solid medium 7 may suddenly be elevated to extreme temperatures (or decreased to extreme temperatures) it is necessary that the buffer 3 be able to sustain a substantial end-to-end thermal gradient and thermal shock in order to protect the electroacoustic transducer 4 from these temperature extremes. Typically, under these circumstances, the ratio of length to diameter of the buffer element 3 would be greater than 10.

In the typical application, the transducer is operated as a clamp-on transducer in which pressure is applied to the block 1 in such a fashion as to force the buffer 3 tightly against the surface 7 to achieve adequate acoustic coupling. This contact pressure can be applied by a set screw from a yoke, or clamp applied against and into the cavity 1a as shown in the block 1. While no yoke or clamp is here illustrated it may typically take a form as described in U.S. Pat. No. 4,286,470. Typically a coupling force in the range of 50 to 500 kg is employed. Such a force can produce sufficient intimacy of contact when a resilient coupling film, as illustrated at 1i is employed between the end face of the buffer 3 and the solid medium 7. Suitable materials for this film are teflon tape less than 25 mm thick, silicone rubber, or soft metal foils such as aluminum or gold. Alternatively the face of the buffer 3 may have a teflon coating bonded to it. For most applications the angle $\theta_1$ between the normal and the long axis of the buffer rod 3 is less than 60°, and may, in fact, be 0°.

With this arrangement it is necessary to transfer the coupling force from the block 1 to the buffer element 3. One method of accomplishing this is employment of loose fitting threads 5, as illustrated. These may be employed with matching internal threads on the housing element 2. In the ideal situation these threads would be relatively loose fitting so that extreme changes in temperature will not cause undue stress on the elements.

In the arrangement as shown, then, sufficient force is applied through the block 1 in the housing 2 to the buffer element 3 at its threaded end to establish good ultrasonic transmissive contact with the solid medium 7. Yet, because the remainder of the buffer element is substantially free mechanically from the housing 2, even drastic changes in the expansion due to thermal effects between the housing 2 and the buffer 3 will not stress the buffer. Even in the local region of the threads, there are no tight fits so that the small differential expansion in the region can readily be accommodated by the threads shown. The axial extent of this thread 5 is typically only about ½ to 3 times the buffer diameter so that it is sufficiently short to keep the differential expansion to a minimum. Using the assembly as illustrated in FIG. 1, employing a level zirconate titanate transducer, temperatures at the surface of the solid medium 7 as high as 300° C. have been successfully tested.

In FIG. 2 a second embodiment is illustrated which is designed to accommodate more extreme temperatures at the surface of the solid medium 7. In this configuration thermal resistance is introduced in the housing in the form of a pipe coupling 22 and the addition of a heat exchanging coil 24. The arrangement of the relatively poor thermal contact between threads of coupling 22 and the housing 2 prevents excessive heat from being removed from the localized regions. In some instances this is desirable because removal of too much heat could perturb thermally the medium 7 or the fluid within the medium 7. Such circumstances could arise, for example, if the fluid contained paraffins which could condense, or if the viscosity of the fluid would be adversely affected by the localized cooling. In the cryogenic application, too much transfer of heat to the cryogen could cause local boiling. In the aforementioned high temperature application cooling can be introduced by circulating cool air or water or other suitable coolant fluid through the coil 24.

In the embodiment of FIG. 2 there is also included a sealed coupling 25 between the transducer 4 and the buffer 3. The lower end of this coupling 25 is bonded to the top end surface of the buffer 3 and the coupling is also sealed around the transducer 4 by welding or otherwise hermetically securing a cap 26 into its top end. The cap 26 typically is pipe-tapped with a ⅛" NPT thread which accepts hermetic feedthroughs or through which a jacketed shielded cable may pass. For example, RG-62 coaxial cable with a heat resistant or corrosion resistant outer jacket may be employed. The cable is retained in the coupling by solder and/or mechanical connections to its high and ground conductors, augmented by epoxy or other strong bonding/potting agents. The cable then may continue to a remote non-hazardous area. A suitable material for this sealing coupling is titanium.

With a configuration as illustrated in FIG. 2 temperatures at the surface of solid medium 7 as high as 360° C. may be tolerated.

In FIG. 3 an alternative form of heat exchanger is shown. In this configuration a heat exchange jacket 34 is sealably attached, as for example, by welding, to the housing 2. The jacket 34 is concentrically mounted with a larger diameter than the housing 2 and is fitted with inlet and outlet ports 36 and 37 to allow a suitable coolant or other heat transfer fluid to be flushed through the cavity. In order to enhance convective heat exchange the jacket 34 may be fitted with heat radiating fins 35.

In some clamp-on flowmeter applications it has been found that line contact between a flat face buffer element and a curved pipe surface is sufficient to provide adequate coupling of the ultrasonic waves. To take advantage of this effect a concentrating buffer element, as shown in FIG. 4 has been developed in which the sides of the buffer element 3 have been chamfered to create angled surfaces 41 and 42 to concentrate incident energy from the transducer upon the bottom surface of the buffer element. This tapered tip configuration may, for example, have a tip dimension of 0.25" wide. Such a configuration can regain some of the efficiency lost when employing a multiple interface sealed coupling such as indicated in FIG. 2. If a chamfered buffer, such as illustrated in FIG. 4, is employed, then the space between the tapered sides of the buffer and the block 1 may be filled with a material which does not couple well acoustically to the buffer. Such material may be introduced, for example, by means of a hole as illustrated at 1b in FIG. 1. Suitable materials include low density, high temperature epoxy or RTV or refractory ceramic adhesive or potting compounds.

While the previous examples have illustrated the mechanical connection between the buffer element as loose screw threads, in FIG. 5 there is illustrated a configuration in which a single shoulder 38 is formed in buffer element 3. A corresponding shoulder or lip on the interior wall of the housing 2 provides for coupling to the buffer element 3 to establish the high pressure contact on the surface of the solid medium.

FIG. 6 illustrates a transducer assembly Particularly suitable for transmitting energy from the electroacoustic transducer 4, which typically would be a shear wave crystal, and converting those waves to plate waves resembling Lamb or Rayleigh waves at the interface between the buffer element 3 and the solid surface 7. In a typical example, the end of the buffer element is formed at an angle to provide an angle of incidence, $\theta_1$, of 45°. Continuing this example, the sleeve 2 may be formed of a ½" schedule 80 pipe nipple 9" long which is screwed tightly into the block 1. The nipple is internally threaded ⅝-11 at the beveled end and is then relieved to a 0.687" I.D. over the rest of its length. This provides a sufficient clearance for differential thermal expansion of the housing relative to the ⅝" diameter by 8" long buffer element 3. Rotation of the buffer 3 is prevented by employing an O-ring 8 or alternatively, the set screw 18 in a tapped hole in the block 1. Again, in this configuration, cooling fins 35 are shown attached to the housing 2.

In FIG. 7 an alternative form of housing assembly is shown. The assembly is similar to that in FIG. 6 but, in this configuration, the pipe nipple is threaded at one end only, and its wall is thick enough, either as originally formed or by welding on an optional pressure pad 2a, so that a separate pressure block is not needed to transfer pressure from the external yoke. In this instance the external yoke may be applied directly, for example, to the optional pressure pad. Also the housing 2 as shown, may be formed of two segments connected by a pipe coupling 22.

While specific dimensions and materials have been set forth in above embodiments, it should be understood that many arrangements of combinations of materials may be employed. For example, a Ti housing may be employed with a boron nitride buffer.

In general the buffer 3 may be used to refractably launch at least 4 principal waves in the adjacent solid medium 7. These, as mentioned earlier, are longitudinal, shear (vertically (SV) or horizontally (SH) polarized), Lamb and Rayleigh waves. The factors determining which of the possible modes actually is launched include: incident sound speed and angle, $c_1$ and $\theta_1$ respectively; sound speed and thickness of the adjacent solid medium, $c_2$ and $x_2$, respectively; frequency f; bandwidth $\Delta f$; coupling; diffraction effects; any other significant boundary conditions; and gradients.

For example, Table 1 lists four different incident angles, each one corresponding to a different mode in an adjacent steel pipe or plate 7 for the following assumed conditions.

$c_1 = 1500$ m/s
$c_2 =$ listed function of wave or mode
$f = 500$ kHz
$x_2 = 4$ mm (0.16 inch)

TABLE 1

Selected values of $\theta_1$ at f = 500 kHz to obtain different waves or modes in a given steel plate, by refraction and/or mode conversion

| Case | Wave or Mode | $c_2$ m/s | $\theta_1$, deg | $\theta_2$, deg (angle of propagation in solid material 7) |
|---|---|---|---|---|
| 1 | Longitudinal | 6000 | 12.5 | 60 |

TABLE 1-continued

Selected values of $\theta_1$ at f = 500 kHz to obtain different waves or modes in a given steel plate, by refraction and/or mode conversion

| Case | Wave or Mode | $c_2$ m/s | $\theta_1$, deg | $\theta_2$, deg (angle of propagation in solid material 7) |
|---|---|---|---|---|
| 2 | SV(shear) | 3300 | 23.2 | 60 |
| 3 | Low Order Lamb Waves ($s_o$, $a_o$, $a_1$) | 3300 | 27.0 | 90 |
| 4 | Rayleigh-like surface wave | 3000 | 25.7 | 90 |

It should be noted that in the configurations thus far illustrated it is desirable that the buffer element 3 protrudes slightly from the housing at the lower end to ensure that bumps or irregularities on the adjacent medium 7 do not lift the housing so much that the buffer itself could be decoupled. A protrusion of the buffer of about 0.1 mm is sufficient. As mentioned previously, in place of the block, a pressure pad 2a may be employed.

Referring now to FIG. 8, the long axis of buffer rod 80 is perpendicular to the plane of the pipe wall 7. The coupling pressure is again applied indirectly, from a housing 82 to the buffer 80 by means of a few threads. The housing 82 may be pressured toward the pipe wall 7 by means of a union-type threaded connector nut 86 which engages with the threaded member 7a welded onto the pipe wall 7.

The other elements of the transducer assembly illustrated in FIG. 8 are similar to their counterparts in previous drawings. In a typical example, the housing 82 can be fabricated from a 9" length of ¾" XX strong SS316 pipe, one end of which is threaded to receive pipe cap 83. Under the pipe cap 83 is mounted electrical connector 84, through which the electrical signals pass to and from the electroacoustic or piezoelectric transducer element 81. A projecting sleeve or collar 82a is engaged by union type locking nut 86 which itself threads onto thread sleeve 7a. The housing 82 may be threaded ⅝-11, for example, over a distance of about ¾" in order to transmit pressure to the pressure coupled end of the ⅝" diameter by 8" long buffer element 80. The housing 82 is relieved to an internal diameter of approximately 0.8" over the rest of its length to allow for differential thermal expansion between the buffer element 80 and the housing 82. A heat exchanger 85 can be employed in order to prevent too much heat from reaching transducer 81.

In FIGS. 9 and 9A a special form of a hybrid clamp-on transducer assembly is shown in which Rayleigh or Rayleigh-like surface waves are preferentially guided along channels which are about as wide as, and which are generally parallel to, boundaries of the square hole 95b in a sleeve or conduit 95a. The circular sleeve 95a includes 2 opposed grooves 90a and 90b into which the ends of the transducer assembly buffer elements 93 and 94 fit. The depth of the channels creates walls of thickness $W_a$ and $W_b$ which are in the range of ½ to 4 wavelengths of the Rayleigh wave in the wall. For example, if the transducer frequency is 500 kHz, the Rayleigh wave length is about 6 mm and $W_a$ and $W_b$ may be in the range of 3 to 24 mm. This configuration allows for effective profile immune area averaging of the flow through the pipe. This arrangement of employing a square shaped tube as a flow cell in order to determine flow over an area is described in detail in U.S. Pat. No. 3,906,791, issued Sept. 23, 1975.

As illustrated in FIG. 9A the flow element may include a port allowing the insertion of a torsional density sensor 109.

Figure 10:
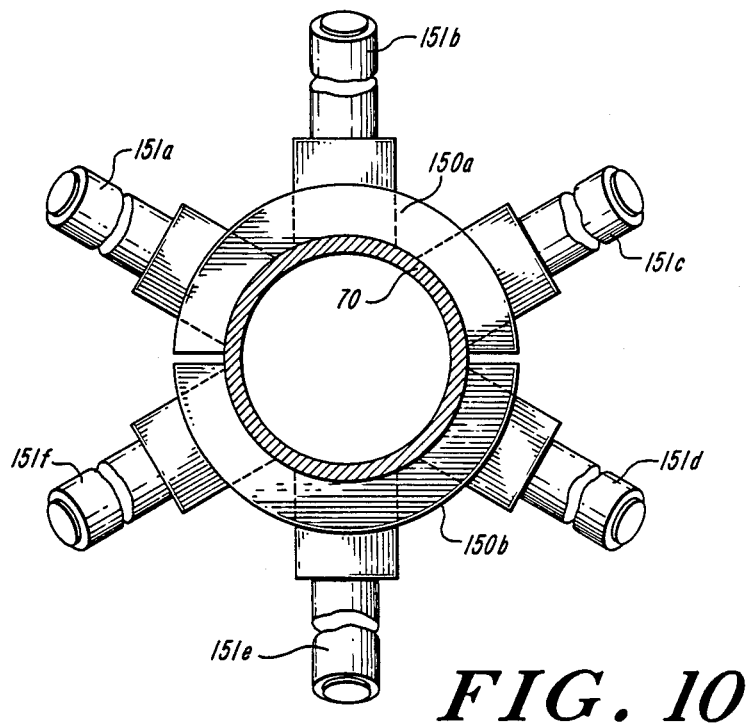
FIG. 10 is a partially perspective view of an array of transducer assemblies suitable for use in the practice of this invention.

While the buffer and transducers of this invention may be installed individually, or in pairs, yet another situation is to arrange the transducers in arrays of multiple units. In FIG. 10 there is illustrated an array which, when viewed in the axial direction, appears as a radial array. The arrangement can be of special importance with respect to measuring liquid in round conduits of small diameter, on the order of 100 mm diameter or less. Such conduits pose special problems for transit time contrapropagation flowmeters because, on a single refracted traverse, the axial interrogation length L is small, typically less than D/2 at high temperature, where D equals the conduit inside diameter. By using a radial array with the transducer elements excited simultaneously, the source of sound approaches a cylindrical or conical source. Ultrasonic waves inside the conduit propagate as a zig-zag radial mode, traveling in the pipe without suffering the same degradation that would occur with a beam which initially is narrow and plane like. With this arrangement the interrogation is along an extended effective axial path Length L' much greater than the diameter D. In addition, a radial array, as illustrated, leads to sampling of the entire cross-section of the fluid, resulting in better precision and higher accuracy despite such variables as cross-flow, swirl or asymmetry in the flow profile.

With reference to FIG. 10 the yoke 150 for this embodiment may be fabricated as a pair of semicircular C-ring clamps. In this configuration three transducers 151a, 151b, and 151c are installed in one semicircular segment 150a, while three additional transducers 151d, 151e and 151f are diametrically aligned with the first three transducers, but mounted in segment 150b. The pipe wall is illustrated at 70. Each of the specific transducer assemblies employed in the configuration of FIG. 10 are formed generally as shown in any of the previous embodiments, particularly, for example, FIG. 1. In a specific example, the buffer diameter may be ⅝", the buffer may have a 45° oblique contact surface with the pipe 70, and the shield can be ⅞" wide at the pressure coupled end.

In some flowmeter applications at temperatures far from ambient, the flow includes swirl. It is possible to measure swirl, or the circulation of a vortex, by measuring non-diametral transit times essentially in a plane perpendicular to the axis of circulation. These transit times should be measured in contrarotating senses, e.g., clockwise (cw) and counterclockwise (ccw). Three midradius chords forming an inscribed equilateral triangle in a round conduit are useful in this regard.

More often the object of a flow measurement is to measure the axial flowrate V independent of the swirl contribution. This is analogous to measuring $V_\phi$, independent of sound speed c. Conventionally, in the absence of swirl, to eliminate c in a contrapropagation flowmeter, travel times are measured upstream and downstream. Similarly, to eliminate $V_\phi$ when swirl is present, transit times should be measured cw and ccw. In some four-path Gaussian quadrature ultrasonic flowmeters, paths are crossed in a cw and ccw manner to eliminate swirl. In the present invention it is proposed to simplify electrical multiplexing or switching and averaging cw and ccw measurements and avoid errors due to lack of simultaneity in multiplexed cw and ccw interrogations, by paralleling cw and ccw measurements, or averaging them by an acoustic method.

Figure 11:
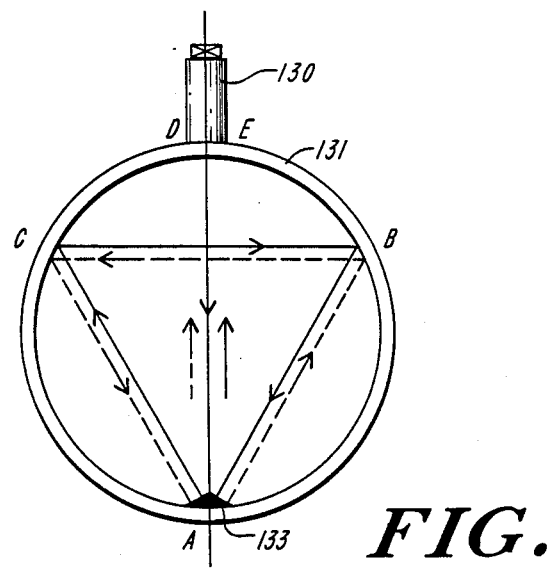
FIG. 11 is a diagrammatic illustration of a specific measurement configuration utilizing a transducer assembly in accordance with the principles of this invention.

In FIG. 11 the simultaneous cw and ccw midradius interrogations are accomplished as follows. A buffered transducer assembly 130 clamped normal to the round pipe 131 at point D transmits a wave across the diameter to a beam-splitting reflector 133 at A. The wave splits into a cw component traversing a triple midradius path ACBA. The wave also splits into a ccw component traversing ABCA. These cw and ccw waves recombine at A and reflect up to D again, if the reflector 133 maintains the cw and ccw paths substantially in one plane, perpendicular to the axis of pipe 131. However, reflector 133 can also be tilted so that the midradius segments are tilted in the axial direction. In this case the cw and ccw waves are reflected off a second reflector located axially downstream in line with the first reflector 133, and then they travel together to a second buffered transducer also displaced axially downstream in line with transducer 130. As long as the time difference due to swirl is not an integer number of half periods, and preferably is less than half a period, the cw and cw components recombine without complete cancellation. Their "average" arrival time tends to produce a received signal representing $c \pm V$ independent of $V_\phi$. The same is true in propagating from E to D. Hence c can be eliminated by the usual upstream-downstream method. The net result is V, the axial component of flow.

While a number of specific examples and configurations have been illustrated, it will be understood that the invention is defined by the attached claims.

I claim:

1. An ultrasonic transducer assembly for transmitting ultrasonic waves to, or receiving ultrasonic waves from a solid surface which is at a temperature differing substantially from ambient, comprising,
    an electroacoustic ultrasonic transducer;
    an elongated buffer element formed of a creep resistant material having predetermined acoustic transmission characteristics and capable of sustaining a substantial temperature gradient along its long dimension, said buffer element having a surface at one end formed for pressurized acoustic coupling to said solid surface, said electroacoustic transducer being acoustically coupled to the opposite end of said buffer element;
    a creep resistant housing of material different from that of said buffer element mechanically coupled to said buffer element over only a small portion of said longitudinal dimension close to the end of said buffer element formed for acoustic coupling to said solid surface, and
    means for applying pressurizing force between said housing element and said solid surface, said mechanical coupling between said housing element and said buffer being such that said pressurizing force is transmitted to said buffer element for establishing a pressurized acoustic coupling between said one end of said buffer element and said solid surface.

2. An ultrasonic transducer in accordance with claim 1 wherein said buffer element is formed as an elongated cylinder and wherein said housing is formed as a hollow tube mounted concentrically with said buffer element, the inner wall of said tube being spaced from the outer surface of said buffer element except at the localized area of mechanical coupling.

3. An ultrasonic transducer assembly in accordance with claim 2 wherein said mechanical coupling is formed by a relatively loose threaded connection between external threads on said buffer element and internal threads on said housing element.

4. An ultrasonic transducer assembly in accordance with claim 2 wherein said mechanical coupling is formed by a shoulder on said buffer element and a cooperating lip extending inwardly from said housing element.

5. An ultrasonic transducer assembly in accordance with claim 2 wherein the portion of said housing element proximate said solid surface is formed as a generally rectangular block having an opening therethrough within which said tubular portion of housing element is fastened.

6. An ultrasonic transducer assembly in accordance with claim 1 and having an ultrasonic transmitting coupling medium positioned between said one end of said buffer element and said solid surface.

7. An ultrasonic transducer assembly in accordance with claim 6 wherein said coupling medium is formed of a resilient material.

8. An ultrasonic transducer assembly in accordance with claim 7 wherein said material is teflon.

9. An ultrasonic transducer assembly in accordance with claim 1 wherein said material is silicon rubber.

10. An ultrasonic transducer assembly in accordance with claim 1 wherein said electroacoustic transducer emits bulk waves along the axis of said buffer element and wherein said buffer element is formed with the end contacting said solid surface having an oblique face for effecting mode conversion of said bulk waves at the interface with said solid medium.

11. An ultrasonic transducer assembly in accordance with claim 1 wherein said buffer element is non-metallic.

12. An ultrasonic transducer assembly in accordance with claim 1 wherein the material of said buffer element is graphite.

13. An ultrasonic transducer assembly in accordance with claim 2 and further including means forming a anti-rotation element positioned between said housing element and said buffer element to prevent rotation of said buffer element within said housing element.

14. An ultrasonic transducer assembly in accordance with claim 1 and further including a heat exchange element positioned surrounding said housing element between the solid medium and the end of said buffer element coupled to said transducer wherein said heat exchange element provides means for maintaining a high temperature gradient along the long axis of said housing element and said buffer element.

15. An ultrasonic transducer in accordance with claim 14 wherein said heat exchange element is a coiled tube containing a heat transfer fluid.

16. An ultrasonic transducer assembly in accordance with claim 14 wherein said heat exchange element is a cylindrical jacket surrounding and spaced apart from the outer wall of said housing element, the interior of said jacket being supplied with a heat transfer fluid.

17. An ultrasonic transducer assembly in accordance with claim 2 wherein said cylindrical housing is formed of two separate portions joined by a thermal resistance element.

18. An ultrasonic transducer assembly in accordance with claim 17 wherein said thermal resistance element is a threaded pipe connection.

19. A ultrasonic transducer assembly in accordance with claim 2 wherein said buffer element is formed with, a tapered end for contacting said solid surface, said end being tapered sufficiently to concentrate transmitted ultrasonic waves to said solid medium through a contact area to said solid surface which is much smaller in width than the diameter of said buffer element.

20. An ultrasonic transducer assembly in accordance with claim 1 in which said buffer element is formed of high acoustic attenuating material for providing high frequency interrogation by repetitive pulses of ultrasonic energy from said electroacoustic transducer.

21. An ultrasonic transducer assembly in accordance with claim 1 and further including a sealed coupling element positioned between said electroacoustic ultrasonic transducer and said buffer element, one surface of said sealed coupling element being in contact with one surface of said electroacoustic ultrasonic transducer and an opposed parallel surface of said sealed coupling element being in contact with one end of said elongated buffer element, said sealed coupling element being formed to provide a sealed enclosure for an electrical connection to said electroacoustic transducer.

22. An ultrasonic transducer assembly in accordance with claim 1 wherein said buffer element is inclined with respect to said solid surface.

23. An ultrasonic transducer assembly in accordance with claim 1 wherein a reflector is disposed for clockwise and counter-clockwise interrogation of a fluid.

24. An ultrasonic transducer assembly in accordance with claim 1 wherein said means for applying pressurizing force includes a block secured to said solid surface, said housing threadedly engaging said block.

* * * * *

UNITED STATES PATENT AND TRADEMARK OFFICE
CERTIFICATE OF CORRECTION

PATENT NO. : 4,783,997
DATED : November 15, 1988
INVENTOR(S) : Lawrence C. Lynnworth It is certified that error appears in the above-identified patent and that said Letters Patent is hereby corrected as shown below:

Column 8, line 61 after "contribution" insert --$V_\phi$.--;

Column 8, line 61 change "$V_\phi$" to --V--.

Signed and Sealed this

Twenty-fourth Day of April, 1990

Attest:

HARRY F. MANBECK, JR.

Attesting Officer     Commissioner of Patents and Trademarks